United States Patent [19]
Hichri et al.

[11] Patent Number: 6,040,477
[45] Date of Patent: Mar. 21, 2000

[54] SULFODECHLORINATING AROMATIC COMPOUNDS

[75] Inventors: Habib Hichri, Snyder; Viesturs Lesins, Buffalo; Christopher C. Sommer, North Tonawanda, all of N.Y.

[73] Assignee: Occidental Chemical Corporation, Dallas, Tex.

[21] Appl. No.: 09/205,409

[22] Filed: Dec. 3, 1998

[51] Int. Cl.$^7$ .......................... C07C 309/32; C07F 11/00
[52] U.S. Cl. ................... 562/46; 562/56; 568/31
[58] Field of Search .................. 562/30, 46, 47, 562/56, 426; 568/31

[56] References Cited

U.S. PATENT DOCUMENTS

| | | | |
|---|---|---|---|
| 2,407,351 | 9/1946 | Stammbach | 260/507 |
| 4,710,322 | 12/1987 | Metz | 562/46 |

*Primary Examiner*—Gary Geist
*Assistant Examiner*—Jean F Vollano

*Attorney, Agent, or Firm*—Anne E. Brookes; Richard D. Fuerle

[57] ABSTRACT

Disclosed is method of sulfodechlorinating an aromatic compound. A composition is prepared of (1) an aromatic compound having the general formula

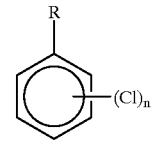

Where R is CHO or COOH and n is 1 to 3, (2) an alkali metal or alkaline earth metal sulfite or bisulfite in an amount stoichiometric to about 20 mole % in excess of stoichiometric, (3) water in an amount sufficient to form a solution of the sulfite or bisulfite, and (4) sufficient base to raise the pH of the composition to about 10 to about 14. The composition is heated at about 150 to about 200° C. No catalyst is present in the composition.

20 Claims, No Drawings

SULFODECHLORINATING AROMATIC COMPOUNDS

BACKGROUND OF THE INVENTION

This invention relates to a process for replacing one or more chlorine atoms on an aromatic ring with sulfonyl groups. In particular, it relates to the reaction of a ring chlorinated aromatic aldehyde or carboxylic acid with a sulfite or a bisulfite in water at a high pH.

The sodium salt of ortho-sulfonylbenzaldehyde (OSBAL) is an important chemical intermediate in the food, dye, and electroplating industries. In DE88952, it is prepared by reacting orthochlorobenzaldehyde (OCBAL) with sodium bisulfite in a neutral medium in an autoclave at 190 to 200° C. and 8 atmospheres pressure (810 kPa) for 8 hours. In DE 2502912, it is prepared by reacting OCBAL with sodium sulfite in an autoclave in the presence of a KI catalyst at 140 to 150° C. and 7 atmospheres pressure (709 kPa) for 3 hours. However, these processes do not produce OSBAL at the desired yield and purity levels.

SUMMARY OF THE INVENTION

We have discovered a process for converting OCBAL into OSBAL that give nearly 100% conversion and nearly 90% yield. In our process, no catalyst is use, so contamination of the product with catalyst is avoided.

DESCRIPTION OF THE PREFERRED EMBODIMENTS

Aromatic compounds useful in the process of this invention are aldehydes and carboxylic acids having the general formula:

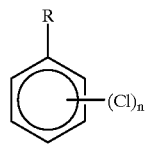

where R is CHO or COOH and n is 1 to 3. Aldehydes are preferred as they are more reactive. In the formula, n is preferably 1 as those compounds are more commercially valuable. The preferred aromatic compound is OCBAL because OSBAL is important commercially.

The aromatic compound is reacted with an alkali metal or alkaline earth metal sulfite or bisulfite. Sodium and potassium sulfites and bisulfites are preferred as they are more stable and sulfites are preferred to bisulfites as they have a higher pH. The amount of alkali metal or alkaline earth metal sulfite or bisulfite present should be about stoichiometric up to about 20 mole % in excess of stoichiometric. The best results are obtained using about 8 to about 12 mole % in excess of stoichiometric.

Sufficient water is used to form a solution of the alkali metal or alkaline earth metal sulfite or bisulfite and keep the reactants in solution during the reaction. Excess water should be avoided as it increases process cost.

Sufficient base is used to raise the pH of the solution to about 10 to about 14. At lower pH's the yield is lower and at higher pH's the reaction mixture is too concentrated; the best results are obtained at a pH between about 11.5 and about 12.5. The preferred bases are alkali metal hydroxides, such as sodium hydroxide and potassium hydroxide, although other bases, such as $Na_2O$, $K_2O$, or $Ca(OH)_2$ can also be used. Preferably, the cation in the base should be identical with the cation in the alkali metal or alkaline earth metal sulfite or bisulfite.

After a composition of the aromatic compound, the alkali metal or alkaline earth metal sulfite or bisulfite, the water, and the base has been prepared, it is placed in an autoclave and is heated to about 150 to about 200° C. At lower temperatures the yield is poorer and higher temperatures may result in the production of byproducts and will require more expensive equipment to contain the higher pressures; a preferred temperature range is about 170 to about 190° C. The pressure will depend upon the temperature and the volume of the autoclave and the quantity of reactants. The reaction can take about 8 to about 16 hours and is faster at higher temperatures. No catalyst is present during the reaction and the product is therefore uncontaminated by a catalyst. The product can be recovered from the reaction mixture by crystallization, extraction, a salting out process, or by other means.

The following examples further illustrate this invention.

EXAMPLE 1

Reactions were performed in a 300 mL autoclave ("Monel" construction) equipped with a self-inducing type agitator, thermocouple, a heating mantle, temperature control, rupture disk, gas inlets and outlets, and a pressure gauge. Into the autoclave was placed a composition consisting of OCBAL, 1.2 equivalents of sodium sulfite, 80 mL of water, 0.0003 moles of catalyst (if used), and sufficient solid sodium hydroxide to reach the desired pH. The autoclave was heated to 190° C. for 6 hours. The following table gives the conditions and results:

| pH | Catalyst | Fractional Conversion | Fractional Yield |
| --- | --- | --- | --- |
| 10 | KI | 0.99 | 0.60 |
| 12 | none | 0.97 | 0.72 |
| 10 | none | 0.84 | 0.81 |
| 12 | KI | 0.89 | 0.68 |

The table shows that the catalyst was of little benefit and actually lowered the yield of OSBAL.

EXAMPLE 2

The following compositions were prepared:

| Composition | $Na_2SO_3$ (g) | OCBAL (g) | $H_2O$ (g) |
| --- | --- | --- | --- |
| 1 | 19.7 | 20 | 160.3 |
| 2 | 26.9 | 20 | 153.1 |
| 3 | 33.3 | 33.7 | 133.0 |
| 4 | 34.8 | 25.9 | 139.3 |

The compositions were placed in the autoclave under the conditions given in the following table:

| Composition | Time (hrs) | T (° C.) | pH | Percent Yield |
| --- | --- | --- | --- | --- |
| 1 | 8 | 150 | 10 | 51 |
| 1 | 16 | 170 | 12 | 78 |
| 2 | 8 | 150 | 12 | 62 |
| 2 | 16 | 170 | 10 | 75 |

-continued

| Composition | Time (hrs) | T (° C.) | pH | Percent Yield |
|---|---|---|---|---|
| 3 | 8 | 170 | 10 | 71 |
| 3 | 16 | 150 | 12 | 71 |
| 4 | 8 | 170 | 12 | 62 |
| 4 | 16 | 150 | 10 | 58 |

The table shows that reaction conditions of 170° C., corresponding to pressure of 115 psig (0.8 MPa), a pH of 12, and reaction time of 16 hours gave the highest yield.

EXAMPLE 3

The compositions of Example 2 were placed in the autoclave. The following table gives the reaction conditions and the results:

| T (C. °) | Time (hrs) | pH | Composition | Fractional Yield |
|---|---|---|---|---|
| 190 | 16 | 12 | 1 | 0.78 |
| 190 | 16 | 12 | 2 | 0.82 |
| 190 | 16 | 12 | 3 | 0.88 |
| 190 | 16 | 12 | 4 | 0.82 |

The table shows that composition 3 had the highest yield.

We claim:

1. A method of sulfodechlorinating an aromatic compound comprising
   (A) preparing a composition of
      (1) an aromatic compound having the general formula:

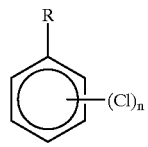

where R is CHO or COOH and n is 1 to 3;
      (2) a sulfur-containing compound selected from the group consisting of alkali metal sulfites, alkali metal bisulfites, alkaline earth metal sulfites, and alkaline earth metal bisulfites, in an amount stoichiometric to about 20 mole % in excess of stoichiometric;
      (3) water in an amount sufficient to form a solution of said sulfur-containing compound; and
      (4) sufficient base to raise the pH of said solution to about 10 to about 14; and
   (B) heating said composition at about 150 to about 200° C. where no catalyst is present in said composition.

2. A method according to claim 1 wherein said aromatic compound is o-chlorobenzaldehyde.

3. A method according to claim 1 wherein said sulfur containing compound is sodium sulfite or potassium sulfite.

4. A method according to claim 1 wherein said sulfur containing compound is a bisulfite.

5. A method according to claim 1 wherein said base is sodium hydroxide.

6. A method according to claim 1 wherein said pH is raised to about 11.5 to about 12.5.

7. A method according to claim 1 wherein the amount of said sulfur containing compound is about 8 to about 12 mole % in excess of stoichiometric.

8. A method according to claim 1 wherein R is CHO.

9. A method according to claim 1 wherein R is COOH.

10. A method according to claim 1 wherein n is 1.

11. A method of sulfodechlorinating an aromatic compound comprising
    (A) preparing a composition of
       (1) an aromatic compound having the general formula

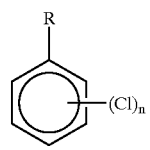

where R is CHO or COOH and n is 1 or 2;
       (2) alkali metal sulfite or bisulfite in an amount about 8 to about 12 mole % in excess of stoichiometric;
       (3) water in an amount sufficient to form a solution; and
       (4) sufficient sodium hydroxide to raise the pH of said composition to about 11.5 to about 12.5; and
    (B) heating said composition at about 170 to about 190° C., where no catalyst is present in said composition.

12. A method according to claim 11 wherein n is 1.

13. A method according to claim 11 wherein R is CHO.

14. A method of making o-sulfonylbenzaldehyde comprising
    (A) preparing a composition of
       (1) o-chlorobenzaldehyde;
       (2) sodium sulfite in an amount about 8 to 12 mole % in excess of stoichiometric;
       (3) water in an amount sufficient to dissolve said sodium sulfite; and
       (4) sodium hydroxide in an amount sufficient to raise the pH of said composition to between 11.5 and 12.5; and
    (B) heating said composition under pressure at about 170 to about 190° C., wherein no catalyst is present in said composition.

15. A method according to claim 1 wherein the cation in said base is the same as the cation in said alkali metal or alkaline earth metal sulfite or bisulfite.

16. A method according to claim 1 wherein said composition is heated in an autoclave.

17. A method according to claim 1 wherein said heating is at about 170 to about 190° C.

18. A method according to claim 1 wherein said heating is for about 8 to about 16 hours.

19. A method according to claim 1 including the additional last step of recovering the product by crystallization, extraction, or a salting out process.

20. A method according to claim 1 wherein said pH is 12.

* * * * *